United States Patent [19]

Grabner et al.

[11] Patent Number: 5,401,645
[45] Date of Patent: Mar. 28, 1995

[54] PROCESS FOR PRODUCING N-SUBSTITUTED POLYHYDROXY NITROGEN-CONTAINING HETEROCYCLES UTILIZING ACETOBACTERACEAE AND CORYNEBACTERIUM

[75] Inventors: Roy W. Grabner, Ballwin; Bryan H. Landis, Manchester, both of Mo.; Mike G. Scaros, Arlington Heights; Rick J. Rutter, Antioch, both of Ill.

[73] Assignees: Monsanto Company, St. Louis, Mo.; G. D. Searle & Co., Chicago, Ill.

[21] Appl. No.: 851,818

[22] Filed: Mar. 16, 1992

[51] Int. Cl.$^6$ .................. C12P 19/02; C12P 19/12; C12P 19/26
[52] U.S. Cl. .................... 435/105; 435/84; 435/99; 435/100; 435/128; 435/170
[58] Field of Search .............. 435/99, 105, 84, 100, 435/128, 170

[56] References Cited

U.S. PATENT DOCUMENTS

| | | | |
|---|---|---|---|
| 3,956,337 | 5/1976 | Niwa et al. | 260/293.86 |
| 4,246,345 | 1/1981 | Kinast et al. | 435/84 |
| 4,266,025 | 5/1981 | Kinast et al. | 435/84 |
| 4,405,714 | 9/1983 | Kinast et al. | 435/84 |
| 4,611,058 | 9/1986 | Koebernick | 546/242 |
| 4,806,650 | 2/1989 | Schroder et al. | 546/242 |
| 4,940,705 | 7/1990 | Boshagen et al. | 514/227.8 |

FOREIGN PATENT DOCUMENTS

| | | |
|---|---|---|
| 0012278 | 6/1980 | European Pat. Off. . |
| 0049858 | 4/1982 | European Pat. Off. . |
| 477160 | 3/1992 | European Pat. Off. . |
| 59-11188A | 1/1984 | Japan . |
| 59-14785A | 1/1984 | Japan . |
| 59-14786A | 1/1984 | Japan . |
| 59-14787A | 1/1984 | Japan . |

OTHER PUBLICATIONS

CA 95(17):148646x–Kinast, G. and Schedel, M., "A four-stage synethesis of 1-deoxynojirimycin with a biotransformation as the central reaction step", *Agnew. Chem.*, 93(9), 799–800 (1981).

CA 111(21):195290k–Von der Osten, C. H. et al., "Use of a recombinaant bacterial fructose-1,6-diphosphate aldolase in aldol reactions: preparative synethesis of 1-deoxynojirimycin, 1-deoxymannojirimycin, 1,4-dideoxy-1,4-imino-D-arabinitol, and fagomine", *J. Am. Chem. Soc.*, 111(11), 3924–7 (1989).

Kagan, et al., "The Preparation of Glycamines", *J. Am. Chem. Soc.*, 79: 3541–3544 (1957).

Mitts, E. and Hixon, R. M., "The Reaction of Glucose with Some Amines", *J. Am. Chem. Soc.*, 66:483–6 (1944).

Mohammed, A. and Olcott, H. S., "Relative Stabilities of D-Glucose-Amine Derivatives", *J. Am. Chem.* 66–969 (1947).

White, S. A. and Claus, G. W., "Effect of Intracytoplasmic Membrane Development on Oxidation of Sorbitol and Other Polyols by *Gluconobacter oxydans*", *J. of Bacteriology*, 150:934–943 (1982).

Rylander, Paul N., "Hydrogenation Methods", *Academic Press*, pp. 82–93 (1985).

Tiwari et al Carbohydrate Research 156 1986 pp. 19–24.

Primary Examiner—Douglas W. Robinson
Assistant Examiner—L. Blaine Lankford
Attorney, Agent, or Firm—Scott B. Feder; Roger A. Williams

[57] ABSTRACT

A process for producing N-substituted amino compounds, a process for oxidizing an N-substituted amino compound with a microbe, or cell fragment or cell free extract thereof, and a process for oxidizing an N-substituted amino compound with a microbe, or cell fragment or cell free extract thereof and reducing the oxidized N-substituted amino compound to N-substituted-polyhydroxy piperidines based on N-substituted mannosamines, allosamines and altrosamines, N-substituted polyhydroxy pyrrolidines, and N-substituted polyhydroxy azetidines. In addition, a one pot process for producing N-substituted-polyhydroxy piperidines based on N-substituted mannosamines, allosamines and altrosamines, N-substituted polyhydroxy pyrrolidines, and N-substituted polyhydroxy azetidines from the respective sugar is disclosed. A second embodiment comprises novel compositions of N-substituted-amino-6-deoxy-2-ketohexuloses based on mannose, allose and altrose, N-substituted-amino-5-deoxy-2-ketopentuloses and 4-(N-substituted)-amino-1,3-dihydroxy-2-butanones.

15 Claims, No Drawings ized with protecting groups. The protecting groups can subsequently be removed by catalytic hydrogenation. Such a process is disclosed in U.S. Pat. No. 4,266,025. In the '025 patent, protected amino sugars are oxidized microbiologically to give protected 6-aminosorboses, which are then isolated. The protective group is then removed by catalytic hydrogenation and the ring is reclosed to form the N-substituted derivatives of 1-deoxynojirimycin. However, the '025 process is a complex process with multiple reaction steps and requires a large amount of catalyst in the hydrogenation step. In addition, the unprotected 6-aminosorboses cannot be isolated as such.

PROCESS FOR PRODUCING N-SUBSTITUTED POLYHYDROXY NITROGEN-CONTAINING HETEROCYCLES UTILIZING ACETOBACTERACEAE AND CORYNEBACTERIUM

BACKGROUND OF THE INVENTION

This invention relates to a process for production of N-substituted polyhydroxy nitrogen-containing heterocycles and intermediates for their production. In one aspect, this invention relates to a process for production of N-substituted polyhydroxy piperidines based on N-substituted mannosamines, allosamines and altrosamines, N-substituted polyhydroxy pyrrolidines, N-substituted polyhydroxy azetidines and intermediates for their production.

A process for the preparation of 1-deoxynojirimycin in which 1-amino-1-deoxyglucitol is oxidized microbiologically to give 6-aminosorbose, which is then hydrogenated with a catalyst to give 1-deoxynojirimycin is disclosed in U.S. Pat. No. 4,246,345. However, the yields of this process, in particular the low volume yields in the microbiological reaction are related to degradation problems and short reaction times, in addition no process for production of N-substituted derivatives of 1-deoxynojirimycin is disclosed.

It is known that N-substituted derivatives of 1-deoxynojirimycin can be made by protecting aminosorbitols with protecting groups which are stable in subsequent microbial oxidations. The protecting groups can subsequently be removed by catalytic hydrogenation. Such a process is disclosed in U.S. Pat. No. 4,266,025. In the '025 patent, protected amino sugars are oxidized microbiologically to give protected 6-aminosorboses, which are then isolated. The protective group is then removed by catalytic hydrogenation and the ring is reclosed to form the N-substituted derivatives of 1-deoxynojirimycin. However, the '025 process is a complex process with multiple reaction steps and requires a large amount of catalyst in the hydrogenation step. In addition, the unprotected 6-aminosorboses cannot be isolated as such.

U.S. Pat. No. 4,405,714 discloses a process for producing N-substituted derivatives of 1-deoxynojirimycin in which glucose is converted into a 1-amino-1-deoxyglucitol. The 1-amino-1-deoxyglucitol is then protected by a protecting group which is stable in the subsequent microbiological oxidation process. The protecting group can then be removed under acid conditions. The compounds are oxidized microbially to give a protected 6-aminosorbose. The protective group on the 6-aminosorbose is then removed under acid conditions. The 6-aminosorbose salt thus obtained is hydrogenated with a catalyst to give the N-substituted derivative of 1-deoxynojirimycin. The '714 process, like the '025 process, is a multistep process which requires the use of protective groups to obtain N-substituted derivatives of 1-deoxynojirimycin.

It has been discovered that N-substituted derivatives of polyhydroxy piperidines based on N-substituted derivatives of mannosamine, allosamine and altrosamine, N-substituted derivatives of polyhydroxy pyrrolidines, and N-substituted derivatives of polyhydroxy azetidines can be made by a process which does not require the use of protecting groups.

SUMMARY OF THE INVENTION

It is an object of the invention to provide a process for preparing the compounds of the invention which does not require the use of protecting groups. It is a further object of the invention to provide an efficient and economic process for preparing the compounds of the invention which is commercially viable.

According to the invention, a process is provided which comprises oxidizing a compound selected from the group consisting of N-substituted-1-deoxy-1-hexosamines based on mannose, allose and altrose, N-substituted-1-deoxy-1-pentosamines, N-substituted-1-deoxy-1-tetrosamines, and salts thereof, with a microbe selected from the group consisting of bacteria of the family Acetobacteraceae, bacteria of the genus Corynebacterium, and cell fragments or cell free extracts thereof, and producing a corresponding compound selected from the group consisting of N-substituted-amino-6-deoxy-2-ketohexuloses based on mannose, allose and altrose, N-substituted-amino-5-deoxy-2-ketopentuloses, 4-(N-substituted)-amino-1,3-dihydroxy-2-butanones, and salts thereof. In one embodiment of the invention, the oxidized product is reduced to produce a compound selected from the group consisting of N-substituted polyhydroxy piperidines based on N-substituted mannosamines, allosamines and altrosamines, N-substituted polyhydroxy pyrrolidines, N-substituted polyhydroxy azetidines, and salts thereof. In a further embodiment of the invention, the material to be oxidized is produced by the amination of a sugar selected from the group consisting of mannose, allose, altrose, ribose, arabinose and erythrose. In a still further embodiment of the invention, a process is provided which comprises converting a sugar selected from the group consisting of mannose, allose, altrose, ribose, arabinose and erythrose to the corresponding reduced product selected from the group consisting of N-substituted polyhydroxy piperidines based on N-substituted mannosamines, allosamines and altrosamines, N-substituted polyhydroxy pyrrolidines, N-substituted polyhydroxy azetidines, and salts thereof.

Further according to the invention, novel compositions of N-substituted-amino-6-deoxy-2-ketohexuloses based on mannose, allose and altrose, N-substituted-amino-5-deoxy-2-ketopentuloses and 4-(N-substituted)-amino-1,3-dihydroxy-2-butanones are provided.

DETAILED DESCRIPTION OF THE INVENTION

A first embodiment of the invention relates to a process for oxidizing a compound selected from the group consisting of N-substituted-1-deoxy-1-hexosamines based on mannose, allose and altrose, N-substituted-1-deoxy-1-pentosamines, N-substituted-1-deoxy-1-tetrosamines and salts thereof, with a microbe selected from the group consisting of bacteria of the family Acetobacteraceae, bacteria of the genus Corynebacterium, and cell fragments or cell free extracts thereof, and producing a corresponding compound selected from the group consisting of N-substituted-amino-6-deoxy-2-ketohexuloses based on mannose, allose and altrose, N-substituted-amino-5-deoxy-2-ketopentuloses, 4-(N-substituted)-amino-1,3-dihydroxy-2-butanones, and salts thereof.

A second embodiment of the invention relates to a process comprising oxidizing a compound selected from the group consisting of N-substituted-1-deoxy-1-hexosamines based on mannose, allose and altrose, N- substituted-1-deoxy-1-pentosamines, N-substituted-1-deoxy-1-tetrosamines, and salts thereof, with an oxidizing microbe selected from the group consisting of bacteria of the family Acetobacteraceae, bacteria of the genus Corynebacterium, and cell fragments or cell free extracts thereof, producing a corresponding compound selected from the group consisting of N-substituted-amino-6-deoxy-2-ketohexuloses, based on mannose, allose and altrose, N-substituted-amino-5-deoxy-2-ketopentuloses, 4-(N-substituted)-amino-1,3-dihydroxy-2-butanones, and salts thereof, and then reducing the oxidized compound to produce the corresponding compound selected from the group consisting of N-substituted polyhydroxy piperidines based on N-substituted mannosamines, allosamines and altrosamines, N-substituted polyhydroxy pyrrolidines, N-substituted polyhydroxy azetidines, and salts thereof.

A third embodiment of the invention relates to a process comprising amination of a sugar selected from the group consisting of mannose, allose, altrose, ribose, arabinose and erythrose to produce the corresponding amino compound selected from the group consisting of N-substituted-1-deoxy-1-hexosamines based on mannose, allose and altrose, N-substituted-1-deoxy-1-pentosamines, N-substituted-1-deoxy-1-tetrosamines, and salts thereof, oxidizing the amino compound with a microbe selected from the group consisting of bacteria of the family Acetobacteraceae, bacteria of the genus Corynebacterium, and cell fragments or cell free extracts thereof, producing a corresponding compound selected from the group consisting of N-substituted-amino-6-deoxy-2-ketohexuloses based on mannose, allose and altrose, N-substituted-amino-5-deoxy-2-ketopentuloses, 4-(N-substituted)-amino-1,3-dihydroxy-2-butanones, and salts thereof, and then reducing said oxidized compound to produce the corresponding compound selected from the group consisting of N-substituted polyhydroxy piperidines based on N-substituted mannosamines, allosamines and altrosamines, N-substituted polyhydroxy pyrrolidines, N-substituted polyhydroxy azetidines, and salts thereof.

A fourth embodiment of the invention relates to a 1-pot process which comprises the steps of (a) mixing a solvent and an amine, (b) adjusting the pH to about 8.0 to about 12.0, (c) adding a sugar selected from the group consisting of mannose, allose, altrose, ribose, arabinose and erythrose in about a 1:1 ratio with the amine, (d) adding a catalyst, (e) reducing at a pressure of about 1 to about 100 atm and a temperature of about 25° C. to about 100° C., (f) removing the catalyst, (g) adjusting the pH to about 1 to about 7, and (h) removing the solvent to obtain the corresponding salt selected from the group consisting of N-substituted-1-deoxy-1-hexosamines based on mannose, allose and altrose, N-substituted-1-deoxy-1-pentosamines, and N-substituted -1-deoxy-1-tetrosamines. The residue containing the corresponding salt is diluted with water and is ready for use in the next step of microbial oxidation without purification.

This can be demonstrated by the following examples.

When D-mannose is used as the starting sugar:

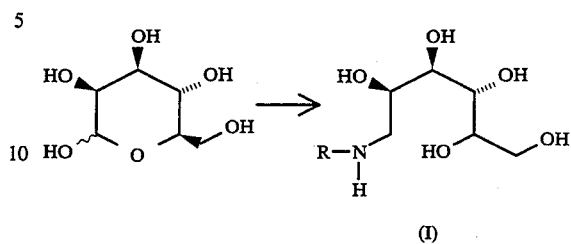

D-mannose    N-substituted-1-deoxy-1-Mannosamine

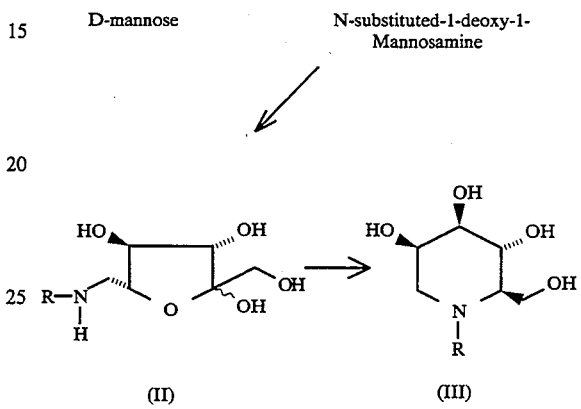

(II)    (III)

6-substituted-amino-6-deoxy-D-fructofuranose    [3R-(3α, 4β, 5β)]-1-(substituted)-2-(hydroxymethyl)-3,4,5-piperidinetriol When E-ribose is used as the starting sugar:

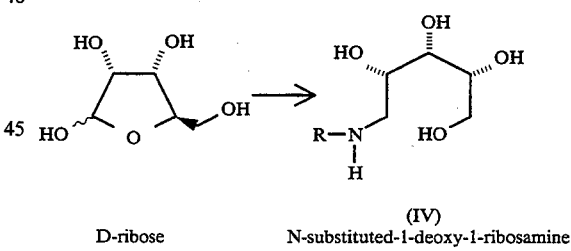

D-ribose    N-substituted-1-deoxy-1-ribosamine

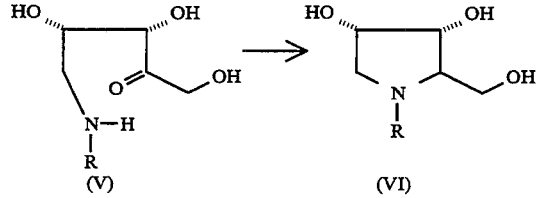

(V)    (VI)

5-substituted-amino-5-deoxy-L-erythro-2-pentulose    1-(substituted)-2-(hydroxymethyl)-(3R-cis)-3,4-pyrrolidinediol When D-erythrose is used as the starting sugar:

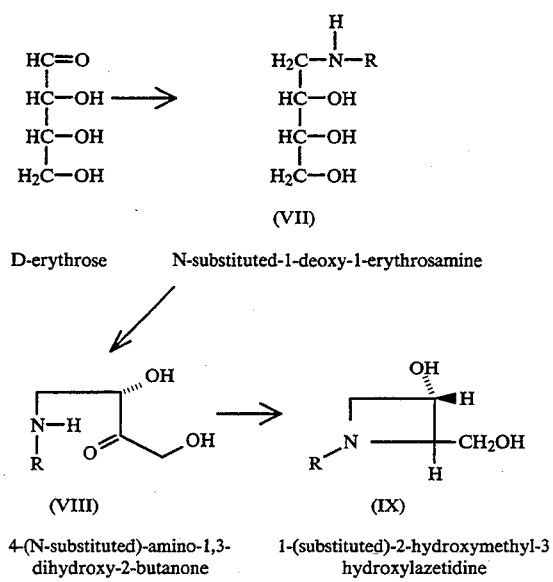

4-(N-substituted)-amino-1,3-dihydroxy-2-butanone 1-(substituted)-2-hydroxymethyl-3-hydroxylazetidine The exact form of the structure of formulas II, V and VIII is dictated by the environment in which the oxidized compound is present (See H. Paulsen et al., Chem. Ber. 100:802 (1967)). The use of the fructofuranose, erythropentulose and butanone nomenclature is not meant to imply that the compound cannot or does not exist in another of its equivalent forms.

The products of the microbial oxidation of the invention are useful as intermediates for producing the N-substituted polyhydroxy piperidines based on N-substituted derivatives of mannosamine, allosamine and altrosamine, polyhydroxy pyrrolidines and polyhydroxy azetidines of the invention which are believed to have utility as antiviral agents, antidiuretics, antidiabetics, animal feed additives and antihyperglycemics.

The substituent on the nitrogen in any of the compounds of the invention is selected from the group consisting of hydrogen, phenyl, $C_1$–$C_{10}$ alkyl, $C_1$–$C_{10}$ alkyl substituted with aromatic, amide or carboxy radicals, and $C_2$–$C_{10}$ alkyl substituted with hydroxy radicals.

Straight chain or branched chain alkyls are suitable to practice the process of the invention, with $C_1$–$C_5$ alkyl groups preferred. Examples of suitable alkyl radicals are methyl, ethyl, n-propyl, 1-methylethyl, n-butyl, 1-methylpropyl, 1,1-dimethylethyl, n-pentyl, 3-methylbutyl, 1-methylbutyl, 2-methylbutyl, n-hexyl, n-heptyl, n-octyl, n-nonyl and n-decyl. Suitable hydroxy substituted alkyl radicals are 2-hydroxyethyl, 3-hydroxypropyl, 4-hydroxybutyl, 5-hydroxypentyl, 6-hydroxyhexyl, 7-hydroxyheptyl, 8-hydroxyoctyl, 9-hydroxynonyl, and 10-hydroxydecyl. Suitable carboxy substituted alkyl radicals are carboxymethyl, 2-carboxyethyl, 3-carboxypropyl, 4-carboxybutyl, 5-carboxypentyl, 6-carboxyhexyl, 7-carboxyheptyl, 8-carboxyoctyl, 9-carboxynonyl and 10-carboxydecyl. Suitable aromatic substituted alkyl radicals are phenylmethyl (benzyl), 2-phenylethyl, 3-phenylpropyl, 4-phenylbutyl, 5-phenylpentyl, 6-phenylhexyl, 7-phenylheptyl, 8-phenyloctyl, 9-phenylnonyl, 10-phenyldecyl and 2-naphthylmethyl. Phenyl alone is also an acceptable radical.

Examples of N-substituted-1-deoxy-1-hexosamines based on mannose, allose and altrose, N-substituted-1-deoxy-1-pentosamines, and N-substituted-1-deoxy-1-tetrosamines of the invention include, but are not limited to:
-benzyl-1-deoxy-1-mannosamine
N-(2-naphthylmethyl)-1-deoxy-1-mannosamine
N-butyl-1-deoxy-1-mannosamine
N-benzyl-1-deoxy-1-altrosamine
N-(2-naphthylmethyl)-1-deoxy-1-altrosamine
N-butyl-1-deoxy-1-altrosamine
N-butyl-1-deoxy-1-allosamine
N-benzyl-1-deoxy-1-allosamine
N-(2-naphthylmethyl)-1-deoxy-1-allosamine
N-benzyl-1-deoxy-1-ribosamine
N-(2-naphthylmethyl)-1-deoxy-1-ribosamine
N-butyl-1-deoxy-1-ribosamine
N-benzyl-1-deoxy-1-arabinosamine
N-(2-naphthylmethyl)-1-deoxy-1-arabinosamine
N-butyl-1-deoxy-1-arabinosamine
N-benzyl-1-deoxy-1-erythrosamine
N-(2-naphthylmethyl)-1-deoxy-1-erythrosamine
N-butyl-1-deoxy-1-erythrosamine Examples of N-substituted-amino-6-deoxy-2-ketohexuloses based on mannose, allose and altrose, N-substituted-amino-5-deoxy-2-ketopentuloses, and 4-(N-substituted)-amino-1,3-dihydroxy-2-butanones, produced by the microbial oxidation process of the invention include but are not limited to:
6-butylamino-6-deoxy-D-fructofuranose
6-benzylamino-6-deoxy-D-fructofuranose
6-(2-naphthylmethylamino)-6-deoxy-D-fructofuranose
6-butylamino-6-deoxy-D-tagatofuranose
6-benzylamino-6-deoxy-D-tagatofuranose
6-(2-naphthylmethylamino)-6-deoxy-D-tagatofuranose
6-butylamino-6-deoxy-L-psicofuranose
6-benzylamino-6-deoxy-L-psicofuranose
6-(2-naphthylmethylamino)-6-deoxy-L-psicofuranose
5-butylamino-5-deoxy-L-erythro-2-pentulose
5-benzylamino-5-deoxy-L-erythro-2-pentulose
5-(2-naphthylmethylamino)-5-deoxy-L-erythro-2-pentulose
5-butylamino-5-deoxy-D-threo-2-pentulose
5-benzylamino-5-deoxy-D-threo-2-pentulose
5-(2-naphthylmethylamino)-5-deoxy-D-threo-2-pentulose
4-butylamino-(S)-1,3-dihydroxy-2-butanone
4-benzylamino-(S)-1,3-dihydroxy-2-butanone
4-(2-naphthylmethyl)-(S)-1,3-dihydroxy-2-butanone Examples of N-substituted polyhydroxy piperidines based on N-substituted mannosamines, allosamines and altrosamines, N-substituted polyhydroxy pyrrolidines, and N-substituted polyhydroxy azetidines that can be produced by hydrogenating the oxidized compounds produced by the microbial oxidation process of the invention include but are not limited to:
1-benzyl-2-hydroxymethyl-[3R-(3α,4β,5β)]-3,4,5-piperidinetriol
1-butyl-2-hydroxymethyl-[3R-(3α,4β,5β)]-3,4,5-piperidinetriol
1-(2-naphthylmethyl)-2-hydroxymethyl-[3R-(3α,4β,5β)]-3,4,5-piperidinetriol
1-benzyl-2-hydroxymethyl-[3R-(3α,4α,5β)]-3,4,5-piperidinetriol
1-butyl-2-hydroxymethyl-[3R-(3α,4α,5β)]-3,4,5-piperidinetriol
1-(2-naphthylmethyl)-2-hydroxymethyl-[3R-(3α,4α,5β)]-3,4,5-piperidinetriol
1-benzyl-2-hydroxymethyl-[3R-(3α, 4α, 5α)]-3,4,5-piperidinetriol 1-butyl-2-hydroxymethyl-[3R-(3α,4α,5α)]-3,4,5-piperidinetriol
1-(2-naphthylmethyl)-2-hydroxymethyl-[3R-(3α, 4α, 5α)]-3,4,5-piperidinetriol
1-benzyl-2-hydroxymethyl-(3R-cis)-3,4,-pyrrolidinediol
1-butyl-2-hydroxymethyl-(3R-cis)-3,4,-pyrrolidinediol
1-(2-naphthylmethyl)-2-hydroxymethyl-(3R-cis)-3,4,-pyrrolidinediol
1-benzyl-2-hydroxymethyl-(3R-trans)-3,4,-pyrrolidinediol
1-butyl-2-hydroxymethyl-(3R-trans)-3,4,-pyrrolidinediol
1-(2-naphthylmethyl)-2-hydroxymethyl-(3R-trans)-3,4,-pyrrolidinediol
1-benzyl-2-hydroxymethyl-3(S)-hydroxyazetidine
1-butyl-2-hydroxymethyl-3(S)-hydroxyazetidine
1-(2-naphthylmethyl)-2-hydroxymethyl-3(S)-hydroxyazetidine The N-substituted amino compounds, i.e. the N-substituted-1-deoxy-1-hexosamines based on mannose, allose and altrose, N-substituted-1-deoxy-1-pentosamines, N-substituted-1-deoxy-1-tetrosamines, and salts thereof, of the invention can be obtained by known means, for example, by amination of the respective sugars. The reductive alkylation of sugars with amines is reported in the literature as a method for preparing N-substituted-1-amino-1-deoxy sugars (see F. Kagan et al., *J. Amer. Chem. Soc.*, 79, 3541 (1957), A. Mohammad et al., *J. Am. Chem. Soc.*, 66, 969 (1947), P. N. Rylander, *Hydrogenation Methods* (Academic Press, (1985) pp. 82–93) and G. Mitts et al., *J. Am. Chem. Soc.*, 66: 483 (1944)). In general these preparations involve reacting a sugar and an amine, in varying ratios, in a suitable solvent such as aqueous methanol or ethanol with an appropriate catalyst such as Raney nickel or palladium on carbon. A catalytic amount of hydrochloric acid is sometimes added. The resulting mixture is hydrogenated under 40–1300 psig of hydrogen pressure at 23°–100° C. for 7–30 hours. The resulting N-substituted amino compound is then isolated.

In a preferred process for preparing N-substituted amino compounds, a Parr shaker bottle, or the like, is charged with a solvent and amine. Suitable solvents include water, alcohols (such as methanol and ethanol) or aqueous alcohols. Preferably the solvent is ethanol. Suitable amines include but are not limited to methyl amine, phenyl amine, ethyl amine, propyl amine, 1-methylethyl amine, n-butyl amine, methylpropyl amine, 1,1-dimethylethyl amine, n-pentyl amine, 3-methylbutyl amine, 1-methylbutyl amine, 2-methylbutyl amine, n-hexylamine, n-heptyl amine, n-octyl amine, n-nonyl amine, n-decyl amine, 2-hydroxyethyl amine, 4-carboxybutyl amine, benzyl amine, 5-phenylpentyl amine, 6-phenylhexyl amine, 7-phenylheptyl amine, 8-phenyloctyl amine, 9-phenylnonyl amine, 10-phenyldecyl amine, 2-(aminomethyl)naphthalene, and 4-(aminomethyl)pyridine. Preferred amines include ethyl amine, n-butyl amine, n-octyl amine, 2-hydroxyethyl amine, benzyl amine, phenyl amine, 2-(aminomethyl)naphthalene and 4-carboxybutyl amine. The ratio of sugar to amine is about 1:1, which allows the product to be used without isolation or removal of excess reagents. The mixture is stirred and cooled while acid is slowly added until a pH in the range of about 8.0 to about 12.0 is obtained, preferably about 9 to about 10.5. Suitable acids include hydrochloric acid, sulfuric acid, nitric acid, acetic acid, ascorbic acid, succinic acid, citric acid, maleic acid, oxalic acid, and phosphoric acid, preferably hydrochloric acid. To the Parr shaker bottle is added the sugar followed by palladium-on-carbon (Pd/C) catalyst (50% water-wet). A palladium catalyst loading of about 1% to about 50% by weight sugar is used, preferably about 10% to about 30%. Catalysts, including but not limited to, Raney nickel, platinum, palladium, rhodium and rhenium, preferably palladium and Raney nickel, can be used. The mixture is agitated and hydrogenated at a pressure of about 1 to about 100 atm, preferably about 3 to about 6 atm of hydrogen and a temperature of about 25° C. to about 100° C., preferably about 40° C. to about 80° C., until the reaction is complete (as indicated by hydrogen uptake). The hydrogen is vented and the palladium-on-carbon removed by filtration (preferably through a layer of powdered cellulose). The catalyst is washed with solvent such as an alcohol, preferably ethanol, followed by washing with water. The washes are combined with the filtrate to give a solution containing a mixture of N-substituted amino compound and its corresponding salt. The solution is cooled to crystallize the amino sugar which is isolated. Alternatively, the mixture is stirred and cooled while hydrochloric acid is slowly added to a final pH of about 1 to about 7, preferably about 4 to about 6. The ethanol is removed by distillation under reduced pressure. The residue contains the salt of the N-substituted amino compound. The residue is diluted with water and ready to use in the next step of microbial oxidation without purification. Thus, the process produces the N-substituted amine compound salts from the respective sugars without isolation or removal of excess reagents. The elimination of isolation and excess reagent removal steps allows for the direct use of N-substituted amino compounds in the microbial oxidation, which oxidation results in the 6-deoxy-6-(N-substituted)-amino-2-hexuloses based on mannose, allose and altrose, 5-deoxy-5-(N-substituted)-amino-2-pentuloses and 4-(N-substituted)-amino-1,3-dihydroxy-2-butanones which in turn can be directly hydrogenated to N-substituted polyhydroxy piperidines based on N-substituted mannosamines, allosamines and altrosamines, N-substituted polyhydroxy pyrrolidines, and N-substituted polyhydroxy azetidines (i.e. one pot process).

An additional advantage of the N-substituted amino compound salts is the elimination of odor associated with residual amines. Typically the amines are extremely odoriferous, requiring the use of respirators when handling. On the other hand, the amino compound salts are relatively odor free, which enables handling without special precautions such as respirators.

As indicated by Material Safety Data Sheets from suppliers of n-butylamine (Fisher Scientific, Fair Lawn, N.J., for example), the n-butylamine compound is toxic and a severe eye, skin and mucous membrane irritant. Exposure to as little as 5–10 ppm of n-butylamine produces nose and throat irritation. Exposure to concentrations of 10–25 ppm are intolerable for more than a few minutes. Thus, the salt forms of the N-substituted amino compounds, which forms do not have the odor and irritation characteristics of the non-salt forms, are advantageous.

To begin the microbial oxidation of an N-substituted amino compound, microorganisms are added to a reaction mixture which comprises an N-substituted amino compound or salts thereof. Alternatively, N-substituted amino compound or a salt thereof is added to cultures of microorganisms that will carry out the oxidation step. Preferably a salt of N-substituted amino compound is added. Suitable salts of N-substituted amino compounds include but are not limited to salts of chloride, sulfate, nitrate, acetate, ascorbate, succinate, citrate, maleate, oxalate, or phosphate. Preferably the hydrochloride salt is used. Although the use of a salt is preferred, a salt can be made in situ by the addition of an N-substituted amino compound and suitable acids to lower the pH and create an N-substituted amino compound salt. During incubation of the reaction mixture containing microorganisms, the reaction is monitored with a reverse phase or ion exchange high performance liquid chromatography (HPLC) assay to observe conversion of N-substituted amino compound to the respective N-substituted-amino-6-deoxy-2-ketohexuloses based on mannose, allose and altrose, N-substituted-amino-5-deoxy-2-ketopentuloses, and 4-(N-substituted)-amino-1,3-dihydroxy-2-butanones. Thin layer chromatography (TLC) and gas chromatography (GC) can also be used to monitor the conversion.

Microorganisms which are suitable for carrying out the oxidation (or microorganisms from which active cell fragments or cell free extracts for carrying out the oxidation are obtained) can be Procaryotae (bacteria), or Eucaryotae, for example fungi, which in each case can belong to diverse taxonomic groups. Suitable microorganisms are found by growing a relatively large number of microorganisms in an appropriate nutrient medium which contains N-substituted amino compounds and examining their ability to produce the oxidized N-substituted amino compounds. The ability of a microorganism to catalyze the oxidation reaction according to the invention can be measured by a variety of means, including assaying with high performance liquid chromatography (HPLC). Microorganisms for use in the process of the invention are readily available from a variety of sources including but not limited to the American Type Culture Collection (ATCC), Rockville, Maryland; the Agricultural Research Culture Collection (NRRL), Peoria, Ill.; Deutsche Sammlung Von Mikroorganismen (DSM), Federal Republic of Germany; and the Fermentation Research Institute (FRI), Japan. Alternatively, a recombinant microorganism can be prepared by isolating or synthesizing the appropriate gene for the oxidizing enzyme and inserting this gene into another microorganism using standard literature techniques such as is disclosed in *Molecular Cloning, A Laboratory Manual,* 2nd Edition, J. Sambrook, E. F. Fritsch, T. Maniatis, eds, Vol. 1,2, and 3, Cold Spring Harbor Laboratory Press (1989).

Examples of suitable microorganisms which are readily available from the above-identified culture collections are bacteria from the order Pseudomonadales and cell fragments or cell free extracts therefrom, bacteria from the family Acetobacteraceae and cell fragments or cell free extracts therefrom, bacteria from the family Coryneform and cell fragments or cell free extracts therefrom, and fungi from the genus Metschnikowia. Within the Pseudomonadales order, preference is for representatives of the family Acetobacteraceae. Within the Acetobacteraceae family, bacteria of the genus Gluconobacter (formerly called Acetobacter) are preferred. Bacteria from the group of Coryneform bacteria, in particular those of the genus Corynebacterium (also known as Curtobacterium), are also suitable. Finally, the oxidation can be carried out with fungi (for example, with yeasts) in particular with those of the family Spermophthoraceae, such as the genus Metschnikowia. In addition, fungi from the genera Agarius and Cephalosporium, and yeasts from the genera Candida and Saccharomyces can be used in the invention.

Examples of suitable Corynebacterium are *Corynebacterium acetoacidophilum, Corynebacterium acetoglutamicum, Corynebacterium acnes, Corynebacterium alkanolyticum, Corynebacterium alkanum, Corynebacterium betae* (also known as *curtobacterium betae*), *Corynebacterium bovis, Corynebacterium callunae, Corynebacterium cystitidis, Corynebacterium dioxydans, Corynebacterium equi, Corynebacterium flavescens, Corynebacterium glutamicum, Corynebacterium herculis, Corynebacterium hoagii, Corynebacterium hydrocarbooxydans, Corynebacterium ilicis, Corynebacterium lilium, Corynebacterium liquefaciens, Corynebacterium matruchotii, Corynebacterium melassecola, Corynebacterium mycetoides, Corynebacterium nephridii, Corynebacterium nitrilophilus, Corynebacterium oortii, Corynebacterium petrophilum, Corynebacterium pilosum, Corynebacterium pyogenes, Corynebacterium rathayi, Corynebacterium renale, Corynebacterium simplex, Corynebacterium striatum, Corynebacterium tritici, Corynebacterium uratoxidans, Corynebacterium vitarumen,* and *Corynebacterium xerosis.* Suitable Gluconobacterium for use in the process of the invention include *Gluconobacter oxydans* subsp. *industrius, Gluconobacter oxydans* subsp. *melanogenes, Gluconobacter oxydans* subsp. *sphaericus,* and *Gluconobacter oxydans* subsp. *suboxydans.* Suitable Acetobacterium for use in the process of the invention include *Acetobacter aceti, Acetobacter hansenii, Acetobacter liquefaciens* (formerly called *Gluconobacter liquefaciens*), *Acetobacter methanolicus, Acetobacter pasteurianus* and *Acetobacter sp.* Metschnikowia (formerly called Candida) preferred for use in the process of the invention include *Metschnikowia pulcherrimia* and yeasts such as *Candida utilis* and *Saccharomyces cerevisiae.*

General growth conditions for culturing the particular organisms are obtained from depositories and from texts known in the art such as Bergey's Manual of Systematic Bacteriology, Vol.1, Williams and Wilkins, Baltimore/London (1984), N. R. Krieg, ed.

The nutrient medium for the growth of any oxidizing microorganism should contain sources of assimilable carbon and nitrogen, as well as mineral salts. Suitable sources of assimilable carbon and nitrogen include, but are not limited to, complex mixtures, such as those constituted by biological products of diverse origin, for example soy bean flour, cotton seed flour, lentil flour, pea flour, soluble and insoluble vegetable proteins, corn steep liquor, yeast extract, peptones and meat extracts. Additional sources of nitrogen are ammonium salts and nitrates, such as ammonium chloride, ammonium sulphate, sodium nitrate and potassium nitrate. Generally, the nutrient medium should include, but is not limited to, the following ions: $Mg^{++}$, $Na^+$, $K^+$, $Ca^{++}$, $NH_4^+$. $Cl^-$, $SO_4^{--}$, $PO_4^{---}$ and $NO_3^-$ and also ions of the trace elements such as Cu, Fe, Mn, Mo, Zn, Co and Ni. The preferred source of these ions are mineral salts.

If these salts and trace elements are not present in sufficient amounts in the complex constituents of the nutrient medium or in the water used it is appropriate to supplement the nutrient medium accordingly.

The microorganism employed in the process of the invention can be in the form of fermentation broths, whole washed cells, concentrated cell suspensions, cell fragments or cell free extracts, and immobilized cells. Preferably concentrated cell suspensions, cell fragments or cell free extracts, and whole washed cells are used with the process of the invention (S. A. White and G. W. Claus (1982), J. Bacteriology, 150: 934–943 and S. Berezenko and R. J. Sturgeon (1991), Carbohydrate Research, 216: 505–509).

Concentrated washed cell suspensions can be prepared as follows: The microorganisms are cultured in a suitable nutrient solution, harvested (for example by centrifuging) and suspended in a smaller volume (in salt or buffer solutions, such as physiological sodium chloride solution or aqueous solutions of potassium phosphate, sodium acetate, sodium maleate, magnesium sulfate, or simply in tap water, distilled water or nutrient solutions). N-substituted amino compound or a salt thereof is then added to a cell suspension of this type and the oxidation reaction according to the invention is carried out under the conditions described.

The conditions for oxidation of N-substituted amino compound in growing microorganism cultures or cell fragments or cell free extracts are similar to those for carrying out the process according to the invention with concentrated cell suspensions. In particular the temperature range is from about 0° C. to about 45° C. and the pH range is from about 2 to about 10. There are no special nutrients necessary in the process of the invention. More importantly, washed or immobilized cells, cell fragments or cell free extracts can simply be added to a solution of N-substituted amino compound or salts thereof, without any nutrient medium present.

The process of the invention can also be carried out with cell fragments or cell free extracts prepared from bacteria. The cell free extracts can be crude extracts, such as obtained by conventional digestion of microorganism cells. Methods to break up cells include, but are not limited to, mechanical disruption, physical disruption, chemical disruption, and enzymatic disruption. Such means to break up cells include ultrasonic treatments, passages through French pressure cells, grindings with quartz sand, autolysis, heating, osmotic shock, alkali treatment, detergents, or repeated freezing and thawing.

If the process according to the invention is to be carried out with partially purified cell fragments or cell free extract preparations, the methods of protein chemistry, such as ultracentrifuging, precipitation reactions, ion exchange chromatography or adsorption chromatography, gel filtration or electrophoretic methods, can be employed to obtain such preparations. In order to carry out the reaction according to the invention with fractionated cell free extracts, it may be necessary to add to the system additional reactants such as, physiological or synthetic electron acceptors, like $NAD^+$, $NADP^+$, methylene blue, dichlorophenolindophenol, tetrazolium salts and the like. When these reactants are used, they can be employed either in equimolar amounts (concentrations which correspond to that of the N-substituted amino compound employed) or in catalytic amounts (concentrations which are markedly below the chosen concentration of N-substituted amino compound). If, when using catalytic amounts, it is to be ensured that the process according to the invention is carried out approximately quantitatively, a system which continuously regenerates the reactant which is present only in a catalytic amount must also be added to the reaction mixture. This system can be, for example, an enzyme which ensures reoxidation (in the presence of oxygen or other oxidizing agents) of an electron acceptor which is reduced in the course of the reaction according to the invention.

If nutrient media is used with intact microorganisms in a growing culture, nutrient media can be solid, semi-solid or liquid. Aqueous-liquid nutrient media are preferably employed when media is used. Suitable media and suitable conditions for cultivation include known media and known conditions to which N-substituted amino compound or salts thereof can be added.

The N-substituted amino compound or salts thereof to be oxidized in the process according to the invention can be added to the base nutrient medium either on its own or as a mixture with one or more oxidizable compounds. Additional oxidizable compounds which can be used include polyols, such as sorbitol or glycerol.

If one or more oxidizable compounds are added to the nutrient solution, the N-substituted amino compound or salts thereof to be oxidized can be added either prior to inoculation or at any desired subsequent time (between the early log phase and the late stationary growth phase). In such a case the oxidizing organism is pre-cultured with the oxidizable compounds. The inoculation of the nutrient media is effected by a variety of methods including slanted tube cultures and flask cultures.

Contamination of the reaction solution should be avoided. To avoid contamination, sterilization of the nutrient media, sterilization of the reaction vessels and sterilization of the air required for aeration should be undertaken. It is possible to use, for example, steam sterilization or dry sterilization for sterilization of the reaction vessels. The air and the nutrient media can likewise be sterilized by steam or by filtration. Heat sterilization of the reaction solution containing the substrates (N-substituted amino compound) is also possible.

The process of the invention can be carried out under aerobic conditions using shake flasks or aerated and agitated tanks. Preferably, the process is carried out by the aerobic submersion procedure in tanks, for example in conventional fermentors. It is possible to carry out the process continuously or with batch or fed batch modes, preferably the batch mode.

It is advantageous to ensure that the microorganisms are adequately brought into contact with oxygen and the N-substituted amino compounds. This can be effected by several methods including shaking, stirring and aerating.

If foam occurs in an undesired amount during the process, chemical foam control agents, such as liquid fats and oils, oil-in-water emulsions, paraffins, higher alcohols (such as octadecanol), silicone oils, polyoxyethylene compounds and polyoxypropylene compounds, can be added. Foam can also be suppressed or eliminated with the aid of mechanical devices.

The time-dependent formation of the oxidized N-substituted amino compounds, i.e., N-substituted-amino-6-deoxy-2-ketohexuloses based on mannose, allose and altrose, N-substituted-amino-5-deoxy-2-ketopentuloses, and 4-(N-substituted)-amino-1,3-dihydroxy-2-butanones, in the culture medium can be followed either by thin layer chromatography or HPLC. Preferably the time-dependent formation of the oxidized N-substituted amino compounds is measured by HPLC.

The oxidized N-substituted amino compound obtained in accordance with the process of the invention is isolated from the reaction solution as follows: The cell mass is filtered off or centrifuged off and the supernatant liquor is passed through a column containing acid ion exchanger and rinsed with an alcohol or water. Elution is then carried out with a base and the eluate concentrated. After adding acetone or the like, the oxidized N-substituted amino compound crystallizes out. If it is intended to carry out further processing of oxidized N-substituted amino compound to N-substituted polyhydroxy piperidines based on N-substituted mannosamines, allosamines and altrosamines, N-substituted polyhydroxy pyrrolidines, and N-substituted polyhydroxy azetidines, isolation and/or recovery is not necessary. For producing N-substituted polyhydroxy piperidines based on N-substituted mannosamines, allosamines and altrosamines, N-substituted polyhydroxy pyrrolidines, and N-substituted polyhydroxy azetidines from oxidized N-substituted amino compound, the clear solution, after removal of the cell mass, is reduced, preferably in the presence of a catalyst.

This aspect of the invention (no isolation and/or recovery necessary) is particularly advantageous because the process proceeds directly from the supernatant liquor resulting from the removal of cell mass of the microbial oxidation reaction solution. Likewise, it is especially advantageous because, unlike prior art processes, no amino protecting group has to be removed. The process of the invention eliminates the need to make and isolate protecting group intermediates and avoids removal of the protecting group to obtain the desired compound. The elimination of these steps results in a more efficient process with greater conversions and overall yields, less equipment and shorter cycle times. The oxidized N-substituted amino compounds also exhibit higher solubility, thus higher concentrations are obtainable, which results in high productivity and higher rates. In addition, the oxidized N-substituted amino compounds have great stability which impedes degradation and resulting byproducts.

Several known means are available for reduction (see for example P. N. Rylander, *Hydrogenation Methods* (Academic Press, (1985) pp 82–93 and *Organic Chemistry*, 3rd edition, Eds James B. Hendrickson, Donald J. Cram, George S. Hammond (McGraw-Hill, Chapter 18, 1970)). These means include metal hydride reduction, catalytic hydrogenation, dissolving metal reduction and electrochemical reduction. In general, to reduce the oxidized N-substituted amino compounds to N-substituted polyhydroxy piperidines based on N-substituted mannosamines, allosamines and altrosamines, N-substituted polyhydroxy pyrrolidines, and N-substituted polyhydroxy azetidines, the oxidized N-substituted amino compound is charged to a flask followed by addition of decolorizing carbon. The stirred mixture is then filtered to remove the carbon. The filtrate is added to a hydrogenation apparatus, such as a Parr Laboratory Reactor, containing a hydrogenation catalyst. Catalyst loading from about 1–100% by weight of the oxidized N-substituted amino compound using Group VIII B metals are used. Preferably about 40–60% is used. Such catalysts include but are not limited to palladium, platinum, nickel and rhodium. Supports for the catalysts may include but are not limited to alumina, barium sulfate, calcium carbonate, carbon, silica and kieselguhr. Typically, the support would contain a 1–20% metal loading, preferably a 4–10% loading. A palladium catalyst is preferred. The mixture is hydrogenated for about 5 hours. Hydrogen pressure from about 1 to about 100 atm can be used; preferably a range from about 1 to about 5 atm is used. The catalyst is then removed and acid ion-exchange resin added to the filtrate to adsorb the N-substituted polyhydroxy piperidines based on N-substituted mannosamines, allosamines and altrosamines, N-substituted polyhydroxy pyrrolidines, and N-substituted polyhydroxy azetidines. The N-substituted polyhydroxy piperidines based on N-substituted mannosamines, allosamines and altrosamines, N-substituted polyhydroxy pyrrolidines, and N-substituted polyhydroxy azetidines are released from the resin and isolated.

When the substituent on the nitrogen of the oxidized N-substituted amino compounds is methyl substituted with aromatic, the oxidized N-substituted amino compounds can be reduced directly to the corresponding N-substituted polyhydroxy piperidines based on N-substituted mannosamines, allosamines and altrosamines, N-substituted polyhydroxy pyrrolidines, and N-substituted polyhydroxy azetidines wherein the substituent on the nitrogen is hydrogen by using catalytic hydrogenation such as with a palladium on carbon catalyst. The corresponding N-substituted polyhydroxy piperidines based on N-substituted mannosamines, allosamines and altrosamines, N-substituted polyhydroxy pyrrolidones, and N-substituted polyhydroxy azetidines wherein the substituent on the nitrogen is methyl substituted with aromatic can be prepared by using metal hydrides as the reducing agent.

The following examples illustrate the specific embodiments of the invention described herein. As would be apparent to skilled artisans, various changes and modifications are possible and are contemplated within the scope of the invention described.

EXAMPLES

Example 1

Preparation of Cell Paste of Microorganisms

A *Gluconobacter oxydans* cell paste is prepared by inoculating a series of 10 liter fermentors, each containing eight liters of media with 60 gm. D-sorbitol-liter, 24 gm. yeast extract/liter, 48 gm. potassium phosphate dibasic/liter and 0.3 ml. antifoam/liter (Ucon LB 625) with the microorganism *G. oxydans* (DSM2003). The fermentors are agitated and aerated while controlling temperature (30° C.) and pH (5.5 to 6.5) during the cell growth period. The fermentations are terminated after about 27 hours when optical density measurements indicate the log growth phase has been completed. The broths are then cooled, centrifuged, and the cells resuspended in water (or 0.02M $MgSO_4$) and centrifuged to produce washed cell paste. These cell pastes are subdivided into aliquots and stored at or below 10° C. until thawed for addition to a reaction solution.

2.90 Grams of N-benzyl-1-deoxy-1-mannosamine were dissolved in 50 mL water and the pH adjusted to 5.0 with concentrated HCl. This solution was filtered through a $0.2\mu$ filter and placed in a sterile 500 mL shake flask. To this were added freshly thawed *Gluconobacter oxydans* cells to give approximately 47 mg/mL (wet cell weight). The shake flask containing the suspension was rotated at 120 rpm, room temperature for 22 hours. At this point the suspension was clarified by centrifugation and filtered through a $0.2\mu$ filter. 13.5 mL of this solution was chilled in ice, the pH adjusted to over 11 with 1.5 mL 2.5N NaOH and reduced with 233 mg $NaBH_4$ at 0° C. for two hours. After standing overnight under refrigeration, the solution was acidified and freeze-dried. After acetylation of a sample with 1:1 triethylamine-acetic anhydride, GC-mass spec indicated the presence of a peak at m/e 422, corresponding to M+H for 1-benzyl-2-hydroxymethyl-[3R-(3α, 4β, 5β)-3,4,5-piperidinetriol tetraacetate.

Example 2

25 mL of the bioconversion solution from Example 1 was reduced with hydrogen and Pd/C at 63 psig, room temperature for 2.5 hours. After lyophilization and acetylation of a sample, GC-mass spec indicated the presence of a peak at m/e 374, corresponding to M+H for 2-hydroxymethyl-[3R-(3α, 4β, 5β)]-3,4,5-piperidinetriol pentaacetate.

Example 3

3.49 Grams of N-(2-naphthylmethyl)-1-deoxy-1-mannosamine were dissolved in 50 mL water and the pH adjusted to 5.0 with concentrated HCl. This solution was filtered through a 0.2μ filter and placed in a sterile 500 mL shake flask. To this were added freshly thawed *Gluconobacter oxydans* cells to give approximately 54 mg/mL (wet cell weight). The shake flask containing the suspension was rotated at 120 rpm, room temperature for 22 hours. At this point the suspension was clarified by centrifugation and filtered through a 0.2μ filter. 12.5 mL of this solution was chilled in ice, the pH adjusted to 8.1 with 1.2 mL 2.5N NaOH, 25 mL of chilled methanol were added and the sample reduced with 318 mg NaBH$_4$ at 0° C. for two hours. After standing overnight under refrigeration, the solution was acidified and freeze-dried. Acetylation of a sample of the dried product gave m/e 472 (M+H) by GC-mass spec, corresponding to 1-(2-naphthylmethyl)-2-hydroxymethyl-[3R-(3α, 4β, 4β)]-3,4,5-piperidinetriol tetraacetate.

Example 4

25 ML of the bioconversion solution from Example 3 was reduced with hydrogen using a Pd/C catalyst at 63 psig, room temperature for 3.5 hours. After lyophilization and acetylation of a sample, GC-mass spec indicated the presence of a peak at m/e 374, corresponding to M+H for the pentaacetate of 2-hydroxymethyl-[3R-(3α, 4β, 5β)]-3,4,5-piperidinetriol.

Example 5

1 Gram of N-butyl-1-deoxy-1-mannosamine was dissolved in 40 mL water and the pH adjusted to 5.0 with HCl, and the volume adjusted to 50 mL. This solution was filtered through a 0.2μ filter and placed in a sterile 500 mL shake flask. To this were added freshly thawed *Gluconobacter oxydans* cells to give approximately 50 mg/mL (wet cell weight). The shake flask containing the suspension was rotated at 120 rpm, room temperature for 48 hours. At this point the suspension was clarified by centrifugation and filtered through a 0.2μ filter and freeze-dried. HPLC assay after 24 hours indicated over 95% conversion to 6-butylamino-6-deoxy-D-fructofuranose.

Example 6

1.5 Grams of N-butyl-1-deoxy-1-arabinosamine hydrochloride was dissolved in 45 mL water and (the pH was 5.35) the solution filtered through a 0.45μ filter and placed in a sterile 500 mL shake flask. To this were added freshly thawed *Gluconobacter oxydans* cells to give approximately 40 mg/mL (wet cell weight). The shake flask containing the suspension was rotated at 120 rpm, room temperature for 48 hours. After 48 hours, the suspension was clarified by centrifugation. After treatment with charcoal, catalytic hydrogenation (4% Pd/C) at 50 psig and acetylation, GC-mass spec indicated the presence of a peak with m/e at 316, consistent with 1-(n-butyl)-2-hydroxymethyl-(3R-trans)-3,4-pyrrolidinediol triacetate.

Example 7

1 Gram of N-benzyl-1-deoxy-1-arabinosamine was dissolved in 45 mL water and the pH adjusted to 5.1 with HCl. This solution was filtered through a 0.45μ filter and placed in a sterile 500 mL shake flask. To this were added freshly thawed *Gluconobacter oxydans* cells to give approximately 40 mg/mL (wet cell weight). The shake flask containing the suspension was rotated at 120 rpm, room temperature for 48 hours, at which time the suspension was clarified by centrifugation. The supernatant was treated with charcoal and catalytically hydrogenated (4% Pd/C) at 50 psig. The reduced product was adsorbed onto Dowex 50X8 (acid form), washed and eluted with NH$_4$OH-methanol. After evaporation of the solvents in vacuo, the residual oil was dissolved in water and lyophilized. GC-mass spec after acetylation indicated the presence of M+H=302, consistent with 2-hydroxymethyl-(3R-trans)-3,4-pyrrolidinediol tetraacetate.

Example 8

0.47 Gram of N-butyl-1-deoxy-1-ribosamine was dissolved in 45 mL water and the pH adjusted to 5.5 with HCl. This solution was filtered through a 0.2μ filter and placed in a sterile 500 mL shake flask. To this were added freshly thawed *Gluconobacter oxydans* cells to give approximately 40 mg/mL (wet cell weight). The shake flask containing the suspension was rotated at 120 rpm, room temperature for 24 hours. At this point the suspension was clarified by centrifugation and filtered through a 0.45μ filter, treated with 1.5 gram of charcoal and catalytically hydrogenated in the presence of 1 gram 4% Pd/C. The hydrogenation product was adsorbed onto Dowex 50X8 (H+ form), then eluted with NH$_4$OH-methanol. After evaporation of the solvents in vacuo, the resulting oil was dissolved in water, the pH adjusted to 6 with HCl and freeze-dried. After acetylation, GC-mass spec indicated the presence of a molecular ion (M+H) at 316, consistent with 1-(n-butyl)-2-hydroxymethyl-(3R-cis)-3,4-pyrrolidinediol triacetate.

Example 9

1 Gram of N-benzyl-1-deoxy-1-erythrosamine was dissolved in 50 mL water and the pH adjusted from 10.23 to 5.21 with HCl. To this solution were added 2 grams *Gluconobacter oxydans* cells and the suspension shaken at 120 rpm, and room temperature. The pH was readjusted to 4.8 to 5.3 as needed. After 24 hours the cells were removed by centrifugation and the supernatant recharged with another 2 grams *Gluconobacter oxydans* cells. After 72 hours the cells were again removed by centrifugation and the supernatant frozen. GC analysis indicated the presence of at least 80% bioconversion of the 1-deoxy-1-N-benzylerythrosamine. After thawing, the yellow supernatant was treated with 1.2 grams activated charcoal (40 minutes) and filtered. The colorless filtrate was adjusted to pH 10.0 with NaOH and hydrogenated with 1 gram 4% Pd/C overnight. This was then filtered to remove catalyst. On standing, crystals formed which were filtered off. After drying the filtrate, acetylation of a portion gave m/e 230 by GC-mass spec, consistent with the triacetate of 2-hydroxymethyl-3(S)-hydroxyazetidine.

Example 10

1.8 Grams of N-butyl-1-deoxy-1-erythrosamine were dissolved in 4 mL water, of which 2 mL were diluted to 50 mL with water; the pH was 5.25. This solution was filtered through a 0.2µ filter and placed in sterile 500 mL shake flask. To this were added freshly thawed *Gluconobacter oxydans* cells to give approximately 40 mg/mL (wet cell weight). The shake flask containing the suspension was rotated at 120 rpm, room temperature for 48 hours. GC analysis of acetylated samples of the clarified suspension indicated the presence of a modified derivative of the 1-deoxy-1-N-(n-butyl)erythrosamine.

Example 11

This example illustrates the use of a cell free extract of *Gluconobacter oxydans*. 61 grams of *Gluconobacter oxydans* cell paste was suspended in 108 grams of water. The cells were disrupted by three passes through a French press at 20,000 psig, giving greater than 95% disruption as determined by microscopic examination. The homogenate was centrifuged at 43,000XG, 2° C., for 3 hours. The supernatant was carefully decanted yielding a cell free extract. The pellet contained the cell fragments. To 50 mL of N-butylmannosamine at approximately 50 grams per liter (assay by HPLC indicated 49 gm/L as the hydrochloride salt) in a 500 mL shake flask were added 3.5 grams of the cell free extract. The shake flask was then rotated at 120 rpm at room temperature for 16 hours, at which time HPLC assay indicated that 39% of the N-butyl-1-deoxy-1-mannosamine had been converted to the corresponding 6-butylamino-6-deoxy-D-fructofuranose.

Example 12

To 50 mL of N-butyl-1-deoxy-1-mannosamine at approximately 50 grams per liter (assay by HPLC indicated 49 gm/L as the hydrochloride salt) in a 500 mL shake flask were added 3.5 grams of the resuspended cell fragments prepared in Example 11. This was rotated at 120 rpm at room temperature for 16 hours, at which time HPLC assay indicated that 99% of the N-butyl-1-deoxy-1-mannosamine had been converted to the corresponding 6-(n-butyl)-amino-6-deoxy-D-fructofuranose.

Example 13

2.5 grams of N-butyl-1-deoxy-1-mannosamine were dissolved in 49 mL water and the pH adjusted to less than 6. This solution was placed in a 500 mL shake flask and 2 grams *G. oxydans* cell paste were added. The shake flask containing the suspension was shaken at 120 rpm at room temperature. After 24 hours, HPLC indicated that all of the N-butyl-1-deoxy-1-mannosamine had been converted to the corresponding 6-butylamino-6-deoxy-D-fructofuranose. Cells were removed by centrifugation and the supernatant treated with charcoal. The filtrate from the charcoal treatment was diluted with 50 mL water and hydrogenated at 50 psi with 2 grams palladium on charcoal for 4 hours at room temperature. After filtering off the catalyst, HPLC indicated reduction to the 1-butyl-2-hydroxymethyl-3,4,5-piperidinetriol.

Example 14

2.8 grams of N-(2-naphthylmethyl)-1-deoxy-1-arabinosamine were dissolved in 50 mL water and the pH adjusted to 5 with hydrochloric acid. This solution was placed in a 500 mL shake flask and 2 grams *G. oxydans* cell paste were added. The shake flask containing the suspension was shaken at 120 rpm at room temperature. After 22 hours the cells were removed by centrifugation. 15 mL of the supernatant was chilled in ice, adjusted to pH 12 with sodium hydroxide diluted with 20 mL methanol and reduced with sodium borohydride. After reduction at refrigeration temperatures the solution was acidified and lyophilized. After acetylation of a sample of the dry powder, GC-mass-spec gave m/e 400 (M+H), corresponding to 1-(2-naphthylmethyl)-2-hydroxymethyl-(3R-cis)-3,4-pyrrolidinediol.

Example 5

This example demonstrates the preparation of N-benzyl-1-deoxy-1-erythrosamine. In a Parr reactor, four grams of erythrose were suspended in 10 mL of benzylamine, 50 mL water and 50 mL methanol. To this suspension was added 5 grams of Raney nickel and the mixture hydrogenated at 50 psi and 50° C. for four hours. the catalyst was filtered off and rinsed with 150 mL water which was combined with the filtrate. The total filtrate was acidified an treated with anion exchange resin. The product was eluted from the resin with methanol-aqueous ammonia, the solvents evaporated in vacuo and the resulting recrystallized from ethanol-ethyl acetate-ether.

Example 16

This example demonstrates the preparation of N-(4-picolinyl)-1-deoxy-1-mannosamine. 15.5 grams of D(+)-mannose were suspended in 9.5 mL 4-(aminomethyl)pyridine and 200 mL methanol. To this suspension were added 5 grams Raney nickel and the mixture hydrogenated at 60 psi and 50° C. for 6.5 hours. The catalyst was filtered off and the solvents evaporated in vacuo. The resulting oil was crystallized from ethanol.

Example 17

This example demonstrates the preparation of N-(4-picolinyl)-1-deoxy-1-arabinosamine. 15.5 grams of D(−)-arabinose were dissolved in 9.5 mL 4-(aminomethyl)pyridine, 135 mL methanol and 65 mL water. To this solution were added 5 grams Raney nickel and the mixture hydrogenated at 60 psi and 50° C. for 6.25 hours. The catalyst was filtered off and the solvents evaporated in vacuo. The resulting oil was crystallized from ethanol.

Although the invention has been described with respect to specific modifications, the details thereof are not to be construed as limitations, for it will be apparent that various equivalents, changes and modifications may be resorted to without departing from the spirit and scope thereof and it is understood that such equivalent embodiments are to be included therein.

That which is claimed is:

1. A process for producing a compound selected from the group consisting of N-substituted-amino-6-deoxy-2-ketohexuloses based on mannose, allose and altrose, N-substituted-amino-5-deoxy-2-ketopentuloses, 4-(N-substituted-amino-5-deoxy-2-ketopentuloses, 4-(N-substituted)-amino-1,3-dihydroxy-2-butanones, and salts thereof wherein the substituent on the nitrogen is selected from the group consisting of phenyl, $C_1$–$C_{10}$alkyl, $C_1$–$C_{10}$ alkyl substituted with aromatic, amide or carboxy, and $C_2$–$C_{10}$ alkyl with hydroxy, comprising contacting, under conditions suitable for microbial oxidation, (i) an N-substituted amino sugar compound selected from the group consisting of N-substituted-1-deoxy-1-hexosamines, based on mannose, allose and altrose; N-substituted-1-deoxy-1pentosamines; N-substituted-1-deoxy-1-tetrosamines, wherein the N-substituted amino sugar compound lacks a nitrogen protecting group; and (ii) (a) microorganisms selected from a group consisting of Acetobacteraceae and Corynebacterium, or (b) a cellular fraction of the microorganisms, the microorganisms or fraction thereof being capable of oxidizing the N-substituted amino sugar compound.

2. The process according to claim 1 wherein said microorganism is bacteria of the genus Gluconobacter.

3. The process according to claim 2 wherein said microorganism is *Gluconobacter oxydans*.

4. The process according to claim 3 wherein said microorganism is *Gluconobacter oxydans* subsp. *suboxydans*.

5. The process according to claim 1 wherein said microorganism is *Corynebacterium betae*.

6. The process according to claim 1 wherein said microorganism is used in the form of a cell suspension.

7. The process according to claim 1 wherein said microorganism is used in the form of immobilized cells.

8. The process according to claim 9 wherein N-benzyl-1-deoxy-1-mannosamine is oxidized to produce 6-benzylamino-6-deoxy-D-fructofuranose.

9. The process according to claim 1 wherein N-(2-naphthylmethyl)-1-deoxy-1-mannosamine is oxidized to produce 6-(2-naphthylmethylamino)-6-deoxy-D-fructofuranose.

10. The process according to claim 1 wherein N-butyl-1-deoxy-1-mannosamine is oxidized to produce 6-butylamino-6-deoxy-D-fructofuranose.

11. The process according to claim 1 wherein N-butyl-1-deoxy-1-arabinosamine is oxidized to produce 5-butylamino-5-deoxy-D-threo-2-pentulose.

12. The process according to claim 1 wherein N-benzyl-1-deoxy-1-arabinosamine is oxidized to produce 5-benzylamino-5-deoxy-D-threo-2-pentulose.

13. The process according to claim 1 wherein N-butyl-1-deoxy-1-ribosamine is oxidized to produce 5-butylamino-5-deoxy-L-erythro-2-pentulose.

14. The process according to claim 1 wherein N-benzyl-1-deoxy-1-erythrosamine is oxidized to produce 4-benzylamino-(S)-1,3-dihydroxy-2-butanone.

15. The process according to claim 1 wherein N-butyl-1-deoxy-1-erythrosamine is oxidized to produce 4-butylamino-(S)-1,3-dihydroxy-2-butanone.

* * * * *